| United States Patent [19] | [11] | 4,386,062 |
|---|---|---|
| Beadle | [45] | May 31, 1983 |

[54] INTRADERMAL HORSE SWEAT TEST

[75] Inventor: Ralph E. Beadle, Baton Rouge, La.

[73] Assignee: Research Corporation, New York, N.Y.

[21] Appl. No.: 173,010

[22] Filed: Jul. 28, 1980

[51] Int. Cl.³ .................. A61K 49/00; G01N 1/00; G01N 33/48

[52] U.S. Cl. .................. 424/9; 424/316; 424/330

[58] Field of Search ............ 424/9, 309, 316, 330

[56] References Cited

PUBLICATIONS

Evans, Proc. Royal Soc. B, vol. 145, 1956, pp.61–83.
Aoki, J Invst. Derm., vol. 33, 1959, pp. 441–443.
Snow, Res. in Vet Sci, vol. 27, 1979, pp. 372–378.
Warndorff, Brid. J. of Derm, vol. 90, 1974, pp. 263–268.
Johnson, Chem Abs, vol. 83, 1975, Ab. No. 161523b.
Kingsley, Chem Abs, vol. 83, 1975 Ab. No. 856x.
Warndorff, Chem Abs, vol. 81, 1974, Ab. No. 99667e.

*Primary Examiner*—Anna P. Fagelson
*Attorney, Agent, or Firm*—Haight & Associates

[57] ABSTRACT

A method for semi-quantitativly determining the ability of horses, mules, donkeys and zebras to sweat, which comprises intradermally administering a series of at least twofold dilutions of at least one pharmaceutical compound having $\beta$-2 stimulator activity and substantially free of $\beta$-1 and $\alpha$-adrenergic activity to such animal, observing the skin over the injection area for the formation of sweat droplets, and identifying anhidrotic animals having inadequate thermoregulatory responses to hot, humid climates by the results thereof.

6 Claims, No Drawings

INTRADERMAL HORSE SWEAT TEST

DESCRIPTION OF THE INVENTION

1. Technical Field of the Invention

This invention relates to a new intradermal technique for semiquantitatively determining the ability of horses to sweat, enabling discrimination between horses which sweat normally and those having anhidrosis, a total or partial decrease in their ability to sweat.

2. Background Art

In many tropical and semi-tropical regions, it is important to identify horses having inadequate thermal regulatory responses to hot, humid climates. Such anhidrotic horses are not able to work or exercise strenuously because of their inability to adequately dissipate body heat in such climates, since sweating is the primary mechanism for heat dissipation in horses. Likewise, a test for determining sweating ability would be useful in monitoring the response to therapy in such animals (e.g., the effect of drug treatment for this or other conditions on sweating ability, as well as the effect of controlling electrolyte balance in the diet) and in screening animals to be sold or worked in such areas as the Southern United States, Panama, Burma, Australia, India, Indonesia, Ceylon (Sri Lanka), Malaya, Puerto Rico and Trinidad. In one study by the present inventor (of horses stabled at a racetrack in southern Louisiana), some 2.5 percent of these horses were found to be anhidrotic year-round, with the percentage increasing to 20-30 percent in the summertime.

Anhidrosis was first described by T. W. Wright and T. C. Tull in Vet. J. 81: 235-239 (1925) and more definitive worked was reported much later by C. L. Evans. T. Aoki et al. in J. Invest. Dermatol. 32: 441-443 (1959) reported on the responsiveness of horse sweat glands to intradermal injections of sudorific agents, including isopropylnoradrenaline which has essentially only $\beta$-1 and $\beta$-2 stimulator activity. However, Aoki's results were inconsistent with those of Evans and unexplainably reported sweat inducement with all agents tried, including both sympathetic and parasympathetic stimulants. Later work by others has failed to confirm that such results are indeed obtainable, and the aberration may be due to the wide range in environmental temperatures (1°-31° C.) at which the experiments were conducted and the plurality of different areas on the horse where observations were made. Furthermore, no attempt was made to relate such results to the presence of anhidrosis. Accordingly, Evans et al.'s comparable study reported in Veterinary Record 69 (1): 67-75 (1957) remains definitive.

In Brit. Vet. J. 112: 117 (1966), Evans discussed physiological mechanisms which underlie sweating in the horse and described the intradermal injection of adrenaline and noradrenaline, attempting to relate the results of such tests to the ability of a horse to sweat. However, both adrenaline and noradrenaline have $\alpha$-components which exhibit vasoconstricting properties, thereby inhibiting blood flow to the skin and possibly diminishing sweating for that reason. This may result in a number of false negative test reports and impair discrimination between horses which sweat normally and those having anhidrosis, a decreased sweating ability. Indeed, M. G. Anderson et al. reported in Research in Veterinary Science 22: 357-360 (1977) that the vasoconstriction of noradrenaline is so strong as to preclude intramuscular administration due to the limited absorption caused by vasoconstriction in the area of the injection.

The control of the sweating mechanism in the horse is more complex than in most other species and different from that in the cow, sheep, goat, dog, etc. D. H. Snow, reporting in Research In Veterinary Science 23: 246-247 (1977) demonstrated that adrenaline-induced sweating is mediated via $\beta$-2 adrenoreceptors in the horse by intravenous infusion of $\alpha$-adrenoreceptor antagonists, followed by infusion of adrenaline. However, the unopposed activity of adrenaline causes very strong vaso-constriction and decreased peripheral circulation, as well as stimulating all of the $\beta$-1 and $\beta$-2 receptors in the body when administered intravenously, e.g. the heart and gastrointestinal tract. Because of the $\alpha$, $\beta$-1 and $\beta$-2 activities of adrenaline, the heart experiences tachycardia with an attendant risk of ventricular fibrillation. In addition, the intestinal tract stimulation decreases intestinal tone and motility, which can induce colic at sufficiently high dosages. Indeed, as noted by Anderson's previously cited report, the intravenous administration of isoproteranol (which has $\beta$-1 and $\beta$-2, but substantially no $\alpha$, activity) lead to a strong increase in the heart's ideoventricular pacemakers, causing tachycardia.

J. G. Kebebinan et al. in Proc. Nat. Acad. Sci. U.S.A. 72: 3735-3739 (1975) noted the problem of tachyphylaxis associated with continual stimulation by adrenaline, which causes a degradation of the response. This can pose a serious problem in a horse which is partially anhidrotic, as stimulation causes the animal to go completely anhidrotic for two weeks, with no sweat whatsoever produced during exercise. This problem seems likely attributed to $\beta$-stimulation via an intravenous mode of injection.

DISCLOSURE OF THE INVENTION

Accordingly, it is a general object of the present invention to provide an improved method for semiquantitatively determining the ability of animals such as horses, etc. to sweat.

Another object of the present invention is to provide such a test in which the stimulators of sweating activity do not exhibit $\alpha$-adrenergic stimulation, e.g. vasoconstrictive activity, so as to distort the sweating ability determined in the test animal.

An additional object of the present invention is to provide a method for the diagnosis and monitoring of anhidrosis.

A further object of the present invention is to provide a method for isolating $\beta$-2 adrenergic activity and its effect on sweating in animals of the genus Equus.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a method for semi-quantitatively determining the ability of horses, mules, donkeys and zebras to sweat, which comprises intradermally administering a series of at least twofold dilution of at least one pharmaceutical compound having $\beta$-2 stimulator activity and substantially free of $\beta$-1 and $\alpha$-adrenergic activity to such animal, observing the skin over the injection area for the formation of sweat droplets, and identifying animals having inadequate thermoregulatory responses to hot, humid climates by the results thereof. β-2 adrenergic stimulators which are substantially free of β-1 and α-adrenergic activity (i,e, cause no statistically significant increase in heart rate or vasoconstriction upon systemic administration) are selected sympathomimetic amine derivatives of β-phenylethylamine characterized by a substituted phenyl ring structure of the following general formula:

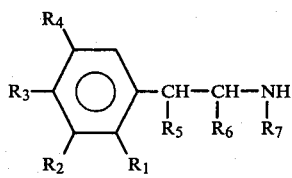

wherein:

$R_1$ is hydrogen or methoxy;
$R_2$ is hydrogen, hydroxy, methoxy or —$NHSO_2CH_3$;
$R_3$ is hydrogen or hydroxy;
$R_4$ is hydrogen, hydroxy, methoxy or a group of the formula:
$R_5$ is hydrogen or hydroxyl;
$R_6$ is hydrogen, methyl or ethyl; and
$R_7$ is hydrogen, methyl, ethyl, isopropyl or isobutyl.

Presently preferred such compounds which exhibit primarily β-receptor stimulation activity include isoproterenol and methoxy-phenamine; especially preferred are such compounds which exhibit primarily β-2 stimulation activity, e.g. terbutaline, clenbuterol, salbutamol, isoetheraine, m-proterenol, fenoterol, ritrodine, soterenol, and quinterenol. These compounds and methods of preparing them are well-known to those skilled in the art, and can generally be used either in the free base form or in the form of a pharmaceutically acceptable acid addition salt.

A basic compound for use in the present invention can be converted into the associated acid addition salt with the use of an acid. For this reaction, suitable acids are those yielding physiologically acceptable salts. Suitable organic and inorganic acids are well known in the art and include but are not limited to aliphatic, alicyclic, araliphatic, aromatic and heterocyclic, mono- or polybasic carboxylic or sulfonic acids, e.g. formic acid, acetic acid, propionic acid, pivalic acid, diethylacetic acid, oxalic acid, malonic acid, succinic acid, pimelic acid, fumaric acid, maleic acid, lactic acid, tartaric acid, malic acid, aminocarboxylic acids, sulfamic acid, benzoic acid, salicylic acid, phenylpropionic acid, citric acid, gluconic acid, ascorbic acid, nicotinic acid, isonicotinic acid, methanesulfonic acid, ethanedisulfonic acid, β-hydroxyethanesulfonic acid, p-toluenesulfonic acid, naphthalene mono- and di-sulfonic acids, sulfuric acid, nitric acid, hydrohalic acids, e.g. hydrochloric acid and hydrobromic acid, and phosphoric acids, e.g. orthophosphoric acid.

The compounds used in this invention are employed in mixture with conventional excipients, i.e., pharmaceutically acceptable organic or inorganic carrier substances suitable for parenteral, enteral or topical application which do not deleteriously react with the active compounds. Generally, the compounds of this invention are employed in serial dilutions of $1-10^{-6}$ mg/ml, preferably $1-10^{-4}$ mg/ml and the quantity administered intradermally to horses is 0.1 ml.

It will be appreciated that the actual preferred amounts of active compounds used will vary according to the specific compound being utilized, the particular compositions formulated, etc. Optimal application rates for a given set of conditions can be ascertained by those skilled in the art using conventional dosage determination tests in view of the above guidelines.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Tenfold serial dilutions of the β-2 stimulator terbutaline were administered in dosages of 0.1 ml and concentrations of $10^{-3}$–$10^{-7}$ g/ml of solution, with a saline control employed, on six different sites of intradermal injections along the necks of 23 horses which were felt by their trainers to be not sweating properly. Each series of injections takes only a few minutes for each horse, and the formation of sweat at the injection sites is essentially complete in about 15 minutes. 18 were determined to be abnormal (only slight positives or "beading" at each dilution, a break point at one of the dilutions beyond which no sweating was stimulated, or all negative). Only five of these 23 horses were all positive at each concentration. In contrast, a control group of 20 normal horses was all positive at each dilution employed.

EXAMPLE 2

Following the same method as in Example 1, horses were similarly tested for anhidrosis in the winter. All but one of the horses showed positive sweat stimulation at each concentration employed. Thus, the problem of anhidrosis normally does not manifest itself except in hot summer months, generally during periods when the temperature at night fails to drop below about 23° C.

EXAMPLE 3

Following the procedures of Example 1, similar results are obtained with other β-2 stimulators.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

As can be seen from the present specification and examples, the present invention is industrially useful in providing a means for discriminating between horses which sweat normally and those having a decreased ability to sweat, thereby facilitating identification of anhidrotic animals and monitoring therapeutic treatment of this condition.

What is claimed is:

1. A method for semi-quantitatively determining the susceptibility of a horse, mule, donkey, or zebra to anhidrosis in climates wherein the temperature at night fails to drop below about 23° C., which comprises:
   (a) Intradermally administering a series of at least two-fold dilutions of at least one pharmaceutical compound having $\beta$-2 stimulator activity and substantially free of $\beta$-1 and a $\alpha$-adrenergic activity to said animal;
   (b) Observing the skin over the injection area for the formation of sweat droplets; and
   (c) Identifying anhidrosis-susceptible animals having inadequate thermoregulatory responses to hot, humid climates by reduced sweat formation at one or more injection sights.

2. A process according to claim 1, wherein said pharmaceutical compound is selected from the group consisting of terbutaline, clenbuterol, salbutamol, isoetheraine, m-proterenol, fenoterol, ritrodine, soterenol, and quinterenol.

3. A method according to claim 2, wherein said pharmaceutical is terbutaline or clenbuterol.

4. A method according to claim 1, wherein said animals are horses.

5. A method according to claim 1, wherein said serial dilutions are tenfold dilutions.

6. A method according to claim 5, wherein said animals are horses and said pharmaceutical compound is terbutaline or clenbuterol.

* * * * *